(12) United States Patent
Chan et al.

(10) Patent No.: US 9,194,780 B2
(45) Date of Patent: Nov. 24, 2015

(54) MICROFLUIDIC PASSIVE MIXING CHIP

(75) Inventors: Eugene Y. Chan, Boston, MA (US); Moon Z Chan, Boston, MA (US)

(73) Assignee: DNA Medicine Institute, Inc., Cambridge, MA (US)

(*) Notice: Subject to any disclaimer, the term of this patent is extended or adjusted under 35 U.S.C. 154(b) by 500 days.

(21) Appl. No.: 13/374,157

(22) Filed: Dec. 14, 2011

(65) Prior Publication Data

US 2013/0260474 A1    Oct. 3, 2013

Related U.S. Application Data

(60) Provisional application No. 61/423,095, filed on Dec. 15, 2010.

(51) Int. Cl.

| G01N 1/38 | (2006.01) |
|---|---|
| B01F 5/00 | (2006.01) |
| B01F 5/06 | (2006.01) |
| B01F 13/00 | (2006.01) |
| B01F 13/10 | (2006.01) |

(52) U.S. Cl.
CPC ............... *G01N 1/38* (2013.01); *B01F 5/0071* (2013.01); *B01F 5/0647* (2013.01); *B01F 13/0059* (2013.01); *B01F 13/0093* (2013.01); *B01F 13/1027* (2013.01); *Y10T 436/25* (2015.01)

(58) Field of Classification Search
CPC ......... G01N 1/38; B01F 5/0647; B01F 5/006; B01F 5/0062; B01F 5/0065; B01F 5/0071; B01F 5/0074; B01F 2005/0017; B01F 2005/002; B01F 2005/0022; B01F 13/0059; B01F 13/1027; B01F 13/1025; B01F 13/0093; B01F 13/0071; Y10T 436/25
See application file for complete search history.

(56) References Cited

U.S. PATENT DOCUMENTS

| 5,691,204 A | 11/1997 | Kim et al. |
|---|---|---|
| 7,160,025 B2 | 1/2007 | Ji et al. |
| 7,294,503 B2 | 11/2007 | Quake et al. |
| 7,595,160 B2 | 9/2009 | White et al. |
| 7,709,544 B2 | 5/2010 | Doyle et al. |
| 2007/0026377 A1 | 2/2007 | Crowe et al. |
| 2008/0153078 A1 | 6/2008 | Braman et al. |

(Continued)

OTHER PUBLICATIONS

Ribeiro, J. C. et al. "A SU-8 fluidic microsystem for biological fluids analysis." Sensors and Actuators A (2005) 123-124 77-81.*

(Continued)

*Primary Examiner* — Christopher A Hixson
(74) *Attorney, Agent, or Firm* — Robert S. Blasi, Esq.; Danielson Legal LLC (57) ABSTRACT

An improved device and method for passive mixing of fluids is described, and the use of the device in clinical diagnostic procedures. The mixer provides thorough mixing of a sample of blood or other fluid with an assay material, such as a diluent or a component of an assay system, in a closed system with a low and limited pressure drop. Sample size is small, typically 5 to 300 microliters. Mixing is accomplished by a combination of rotational vortex mixing due to a fluid stream coming tangent to a drain, and either or both of a second vortex mixer of opposite handedness, and a Dean mixer. Combinations of these techniques reliably provide complete mixing at low pressure drop. In a preferred usage, the microfluidic system can run a diluent continuously and inject samples at intervals, to facilitate automatic data processing of optical or other signatures of the well-mixed stream.

19 Claims, 6 Drawing Sheets

(2 of 6 Drawing Sheet(s) Filed in Color)

(56) References Cited

U.S. PATENT DOCUMENTS

| | | |
|---|---|---|
| 2012/0070833 A1 | 3/2012 | Wang et al. |
| 2012/0190040 A1 | 7/2012 | Talebpour et al. |
| 2012/0214224 A1 | 8/2012 | Chan |
| 2012/0244529 A1 | 9/2012 | Fuchs et al. |

OTHER PUBLICATIONS

Xi, Chuanwu et al. "Structural and functional imaging of 3D microfluidic mixers using optical coherence tomography." PNAS (2004) 101 7516-7521.*

Caldwell, K.D., "Field-Flow Fractionation," 60 Analytical Chem. 17, Amer. Chem. Soc'y. pp. 959A-971A (1988).

Chen and Jang, "Recent Patents on Micromixing Technology and Micromixers," 2 Recent Patents on Mechanical Engineering, pp. 240-247, Bentham Science Publishers Ltd. (2009).

Chow, E.Y.D. et al., "Evaluating the CELL-DYN® 3500 haematology analyser in an acute genertal hospital," 18 Clinical & Lab. Haematology, pp. 187-193, Blackwell Science Ltd. (1996).

Chu, B., "Characterization of Polymer Molecular-Weight Distribution (Particle Sizing)," Laser Light Scattering, pp. 283-285, Dover Publications (2007).

Chung, S. et al., "Plastic Microchip flow cytometer based on 2- and 3-dimensional hydrodynamic flow focusing," 9 Microsystem Tech., pp. 525-523, Springer-Verlag (2003).

Gupta, A. et al., "Use of the HemoCue® near patient testing device to measure the concentration of haemoblobin in suction fluid at elective Caesarean section," 63 J. Assoc. Anaesthetists of Great Britain and Ireland, pp. 531-534, The Association of Anathetists of Great Britain and Ireland (2008).

Hairer, G. et al., "Analysis of Micrometer Sample Flows in a Non Coaxial Sheath Flow Device," 14th Intl. Conf. on Solid-State Sensors, Actuators and Microsystems, pp. 1845-1848, Lyon, France (Jun. 10-14, 2007).

Howell, P.B., Jr. et al., "Two simple and rugged designs for creating microfluidic sheath flow," 8 Lab on a Chip, pp. 1097-1103, The Royal Society of Chemistry (2008).

Huang, S.H. et al., "A monolithically three-dimensional flow-focusing device for formation of single/double emulsions in closed/open microfluidic systems," 16 J. Micromech. and Microeng., pp. 2336-2344, IOP Publishing Ltd. (2006).

Kass, L., "Staining of Granulocyte Cells by Chlorazol Black E," 76 Am. J. Clinical Path. 6, pp. 810-812, American Society of Clinical Pathologists (1981).

Kubitschek, H.E., "Distortion in Coulter Counters and the Applicability of the Sollins-Richmond Principle," 11 Biophys. J., pp. 124-126 (1971).

Kummorow, A. et al., "Microfluidic structures for flow cytometric analysis of hydrodynamically focussed blood cells fabricated by ultraprecision micromachining," 9 Lab on a Chip, pp. 972-981, The Royal Society of Chemistry (2009).

Lebaron, P. et al., "Effectiveness of SYTOX Green Stain for Bacterial Viability Assessment," 64 App. and Envir. Microbiology 7, pp. 2697-2700, American Society for Microbiology (Jul. 1998).

McMurdy, J.W. et al., "Noninvasive Optical, Electrical, and Acoustic Methods of Total Hemoglobin Determination," 54 Clin. Chem. 2, pp. 264-272 (2008).

Miyake, R. et al., "Investigation of Sheath Flow Chambers for Flow Cytometers (Micro Machined Flow Chamber with Low Pressure Loss)," 40 JSME Int. J. 1, Series B, pp. 106-113 (1997).

Morgan, H. et al., "3D focusing of nanoparticles in microfluidic channels," 150 IEE Proc.—Nanobiotechnol. 2, pp. 76-81 (Nov. 2003).

Morimoto, Y. et al., "Three-dimensional axisymmetric flow-focusing device using stereolithography," 11 Biomed. Microdevices, pp. 369-377, Springer Science + Business Media LLC (2009).

Munoz, M. et al., "Utility of point-of-care haemoglobin measurement in the HemoCue-B haemoglobin for the initial diagnosis of anaemia," 27 Clin. & Lab. Haematology, pp. 99-104, Blackwell Publishing Ltd. (2005).

Osei-Bimpong, A., "Point-of-care method for total white cell count: an evaluation of the HemoCue WBC device," 31 Int. J. Lab. Hematology, pp. 657-664, Blackwell Publishing Ltd. (2009).

Pregibon, D. et al., "Multifunctional Encoded Particles for High-Throughput Biomolecule Analysis," 315 Science, pp. 1393-1396 (2007).

Rodriguez-Trujillo, R. et al., "High-Speed particle detection in a micro-Coulter counter with two-dimensional adjustable aperture," 24 Biosens. and Bioelec., pp. 290-296, Elsevier B.V. (2008).

Scott, R. et al., "Three-dimensional hydrodynamic focusing in a microfluidic Coulter counter," 79 Rev. Scientific. Instr., p. 046104-3 (2008).

Shapiro, H., "Identification of Cells in Mixed Populations," Practical Flow Cytometry, 4th Ed., pp. 464-465, Wiley-Liss (2003).

Sheehan, H.L. et al., "An Improved Method of Staining Leucocyte Granules with Sudan Black B," LIX J. Path. Bact., Plate XLVI, pp. 336-337.

Simonnet, C. et al., "Two-dimensional hydrodynamic focusing in a simple microfluidic device," 87 Appl. Phys. Lett., pp. 114104-1-114104-3, AIP Publishing (2005).

Sundarsan, A.P. et al., "Multivortex Micromixing," 103 Proc. Natl. Acad. Sci. U.S.A. 19, pp. 7228-7233, National Academy of Sciences (2006).

Sudarsan, A.P. et al. Fluid mixing in planar spiral microchannels, 6 Lab on a Chip, pp. 74-82, The Royal Society of Chemistry (2006).

Sundararajan, N. et al., "Three-Dimensional Hydrodynamic Focusing in Polydimethylsiloxane (PDMS) Microchannels," 13 J. Micromech. Sys. 4, pp. 559-567, IEEE (Aug. 2004).

Tarnok, A., "SYTO Dyes and Histoproteins—Myriad of Applications," 73A J. Intl. Soc. for Advancement of Cytometry, pp. 477-479 (2008).

Vykoukal, J. et al., "Dielectrophoresis Based Micro Flow Cytometry," Micro Total Anal. Syst., pp. 1153-1156 (2003).

Yang, S. et al., "A microfluidic device for continuous, real time blood plasma separation," 6 Lab on a Chip, pp. 871-880, The Royal Society of Chemistry (2006).

Yang, R. et al., "Microfabrication and Test of a Three-Dimensional Polymer Hydro-focusing Unit for Flow Cytometry Applications," 118 Sens. Actuators A Phys., pp. 259-267 (2004).

* cited by examiner

Figure 1

1. Diffusion

$$J_x = -D \cdot (\partial c/\partial x)_t$$

2. Dean mixing

Sudarson & Ugaz Lab on a chip 2006, 6, 74-82

$$D_n = \delta^{1/2} Re$$

$D_n \sim 1$, transverse pertubation $D_n \sim 10$, significant transverse flows

3. Vortex mixing $$\omega = (x, t)$$

TOP VIEW

SIDE VIEW

3D VIEW inlet outlet

MICROFLUIDIC PASSIVE MIXING CHIP

This application claims the benefit of the priority of U.S. provisional application 61/423,095, filed Dec. 15, 2010, which is incorporated herein by reference in its entirety.

This invention was made with government support under contract # NNX09CA44C awarded by the National Aeronautics and Space Administration and grant #1 R43 HL 099092-01 by the National Institutes of Health. The Government has certain rights in the invention.

BACKGROUND OF THE INVENTION

A system is being developed for clinical analysis using components that are significantly smaller than current analysis systems, and suitable for use in remote environments such as space flight. Current systems for assaying medically-relevant parameters of blood typically require taking one or more venous blood samples, which are then analyzed in one or more large, specialized clinical autoanalyzer systems. The systems, besides being bulky, generate significant volumes of medical waste, which must be treated as a hazardous material.

Moreover, current systems are often highly automated, and have dedicated staff to manage the flow of samples through the machine. Such systems are well adapted to hospitals and clinics. However, there are numerous situations which require more flexibility in a clinical analyzer, and some situations have a relatively low volume of sampling, requiring an analyzer which is suitable for intermittent use. Such requirements may be presented by isolated populations or locations.

Such a machine must be "robust" in operation, so that it can be used without extensive training. Moreover, it should avoid or minimize the amount of waste generated by minimizing the need for large samples and flexibly running multiple assays on a single small sample—for example, a finger prick vs. a sample from a vein. In addition, the system should have the ability to be used only intermittently, rather than daily or continuously as in most current analyzers. The system should also be flexible to allow a wide variety of assays to be analyzed.

One important part of a system for accomplishing these objectives is a device and a method to accomplish all of the steps needed for measurement of clinical parameters, including sample dilution, mixture of a sample with reagents, and delivery of the diluted sample to a flow cell for quantification of one or more parameters. Another important aspect of the system is the ability to work with small samples of blood or other bodily fluid, with sample volumes in the sub-milliliter range, for example 3 to 100 microliters. A related aspect of the system is the ability to perform continuous fluid flow at low differential pressures, to prevent leakage of components and for safety. Such a device is the subject of the present invention.

Another important requirement for the handheld diagnostic system is the need for mixing a blood sample with a stream of analytical reagents. In particular, there is a need for inline mixing in the instrument of the invention. A small sample—typically 3 to 100 microliters, for example from a finger prick—is optionally diluted and fed into an analyzer of the invention.

There are several methods described in the art for mixing microfluidic streams in a flow chamber. These are briefly discussed in Chen and Jang ("Recent Patents on Micromixing Technology", *Recent Patents on Mechanical engineering* 2009, 2, 240-247).

A first alternative is a Dean effect spiral, as described for instance in Ji et al (U.S. Pat. No. 7,160,025) and Sundarsan and Ugaz (US 2007/026377A1). When streams of two fluids of similar properties are brought together non-turbulently, they mix primarily by diffusing. This is a slow process. The process can be accelerated by using "Dean Mixing" in a curved path. In a curved path, mixing occurs even in a laminar flow regime. The Dean effect is non-turbulent and so has a relatively low pressure drop. However, it still takes a significant length of flow path, with a corresponding cost in pressure drop.

A second alternative is an expansion effect in a stream, as described in Sudarsan & Ugaz PNAS 103 (19) 7228-7233; 2006). In this system, a sudden expansion of channel cross section, and if required a subsequent return to a small diameter channel, can mix fluid streams in a short path length. However, the flow tends to be turbulent, causing a relatively high pressure drop in a short distance, and requiring extended rinsing times during cleaning, because the flow is not predictable.

A third alternative is a three dimensional vortex mixer, which has one or more out-of-plane channels for generating transverse flows (Lin et al, J Micromech Microeng. 15 935-943, 2005). In an embodiment useful in the present invention, flow enters through a narrow channel into the beginning of a larger channel which is oriented at a right angle (or other non-obtuse angle) to the flow in the narrow channel. Flow initially spirals around the wall of the larger channel and gradually becomes a flow moving along the larger channel.

A fourth alternative, related to the vortex mixing system, is an out-of-plane drop, approximately equivalent to a right-angle bend. If the path diameter changes substantially, it can be equivalent to a vortex. However, if the bend is sharp and diameter change is limited, it can produce turbulent mixing with relatively low pressure drop. Like other systems having turbulence, abrupt random changes in pressure and flow rate can occur.

Many micromixers for on-chip mixing have been developed based on different mechanisms to disturb the laminar flow (Nguyen and Wu, 2005; Ottino and Wiggins, 2004). These micromixers can be divided in to two groups: passive and active micromixers (Nguyen and Wu, 2005). Active mixers rely on some form of external force to generate a chaotic flow pattern in the microchannel. Some typical external sources are pressure, temperature, electrohydrodynamics, dielectrophoresis, electrokinetics, magnetohydrodynamics and acoustics. The requirement of external power sources for active micromixers makes them less feasible for most point-of-care applications. Passive micromixers rely on geometrical layout of the microchannels to cause lamination and/or chaotic advection (Ansari et al., 2010; Chen and Meiners, 2004; Munson and Yager, 2004; Stroock et al., 2002b; Sudarsan and Ugaz, 2006a, b). Lamination-based designs split the streams and rejoin them after a certain distance, thus increase total contact area between streams (Ansari et al., 2010; Munson and Yager, 2004). The staggered-herringbone design is arguably the most visible one of chaotic advection designs (Stroock et al., 2002b). Changing of flow resistance at different directions causes the streams to rotate inside the channel. However, despite its effectiveness on mixing, the staggered-herringbone grooves can potentially trap blood cells and has been used in this manner for cancer cells (Stroock et al., 2002a). Other designs include planar spiral microchannels tested by Sudarsan and Ugaz (Sudarsan and Ugaz, 2006a, b). Secondary Dean flow occurs in spiral microchannels due to their curvature, while the sudden expansion of the channel causes vortices. Mixers with three-dimensional vortex micromixers have also been utilized to generate transverse flows for rapid mixing. One such approach mixes fluids from eight individual channels tangent to a three-dimensional circular chamber (Lin et al., 2005). Other approaches have demonstrated different number of tangential inlets, from one (Long et al., 2009) to as many as sixteen (Bohm et al., 2001).

We have found that it is advantageous to combine more than one type of mixer into a sample mixing path, particularly for use in a device such as a hand-held diagnostic machine, in which weight and volume are both constrained. When properly designed and proportioned, a path can be constructed that mixes two streams (sample and analytical reagents) in a short distance at low pressure drop.

A related feature of the devices of the invention is an inlet port that minimizes differences in sample dilution, and the effect of variances in dilution, when samples of varying volume are fed into the system. A significant portion of the variance in dilution can be achieved by proper construction of the inlet into the system, so that approximately identical volumes of sample and reagents are mixed on entry.

SUMMARY OF THE INVENTION

The present invention comprises means for the mixture of fluids in a diagnostic system which minimizes system pressure drop while providing good mixing, controlled flow, and great flexibility. The mixing device of the invention has at least two mixing zones. In the passage through these zones, sample is diluted and mixed with appropriate reagents. The system has means for adapting the degree of dilution prior to the analytical step, and in particular has a novel means of controlling dilution by ratiometric metering of sample and diluents into the mixer. The system has characteristic flow path diameters in the range of a few millimeters down to fractions of a millimeter. The preferred system has at least one zone in which mixing occurs by rotational vortex mixing, and a second mixing zone containing one or both of a second vortex mixer and a Dean mixer using a curved spiral path.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

A number of components contribute to the efficacy of the diagnostic system of the invention. One such component is an efficient, reliable, and compact system for mixing samples with diagnostic reagents and passing the mixtures through an optical detection system for reading. This application describes such a system.

One objective of this invention is to provide methods and devices for the efficient dilution of clinical samples, with diluents or with analytical reagents, in a system with minimal use of disposables. In particular, analysis of blood samples is described.

Another objective is a clinical analysis system with sample volumes in the sub-milliliter range. Another objective is to minimize the number of instruments required to obtain the desired clinical values. Another objective is to minimize instrument volume and weight, ideally reducing these parameters sufficiently for portable or preferably hand-held range. Another objective is to create a high level of automation to minimize training needs for operators.

In the course of achieving these objectives, we have developed an efficient system of sample mixing and dilution. In this system, a small clinical sample is applied to a system inlet and is co-injected with a diluent fluid, typically containing analytical reagents, into a mixing section, and then into passage through an optical detection cell.

Initial mixing of these fluids can be laminar, minimizing entrance pressure drop. Dean (geometric) mixing in a curved channel then produces an effective sample dilution of 1:1, 1:5, 1:10, or up to 1:200 or more. Final dilution (when required) and uniformity are then achieved by vortex rotational mixing, achieved in the present invention by a channel tangent to a drain opening. This procedure may be called the "3D vortex" herein.

The resulting device has a low pressure drop, simplifying sample injection. The device is not dependent on precision in the applied volume of clinical sample, both because initial dilution of the sample is approximately independent of the volume entered into the system, and also because the detection system can be calibrated to detect parameters independently to determine the level of dilution.

Another advantage of some embodiments of the system is that the flow cell in which dilution is made can also contain an optical detection system, in which desired clinical parameters can be obtained. Another advantage of the system is that the flow cell is self cleaning.

In one aspect of the invention, a microfluidic mixing device for mixing a sample with a diagnostic reagent is characterized in having reliable mixing and flow at low pressure drop. The device comprises a first section wherein flow is though a spiral channel, and partial mixing is accomplished by Dean mixing; and a second section wherein flow is through at least one vortex mixer, comprising substantially tangential injection of the reagent and the sample into a cavity having a larger diameter than said spiral channel.

The microfluidic mixing device may provide tangential injection at right angles to the substantially circular region of the cavity. The second section is downstream of said first section, and may comprise more than one vortex mixer. It is used for analysis of samples to obtain clinical information, and especially for analysis of samples to diagnose a disease or medical condition.

The device contains a diagnostic fluid that may contain means for analysis of more than medically relevant property of said sample. Preferably, the pressure drop across said device is less than about 5 psi or its equivalent in SI units.

The mixing device preferably has an outlet leading to an analysis region.

It preferably is reusable, after in-line cleaning. It has an inlet shaped to allow substantially laminar flow of sample and reagent into the device, and may be cleaned for re-use by flowing said reagent through said device.

The device is used in analysis of clinical samples, by a method comprising the steps of connecting a first inlet to a supply of a diagnostic fluid, and
connecting a second inlet to a sample to be analyzed, wherein said first and second inlets are connected to a microfluidic mixing device for mixing a sample with a reagent. The use is characterized in that the microfluidic mixing device comprises a first section wherein flow is though a spiral channel, and partial mixing is accomplished by Dean mixing; and a second section wherein flow is through a vortex mixer, comprising substantially tangential injection into a larger diameter substantially circular cavity having an outlet at approximately right angles to the substantially circular region of the cavity.

The method of use further comprises providing a third section downstream of both said first section and said second section, said third section containing one or more devices to perform at least one analysis on the mixture of the fluids from said first and second inlets; and passing said mixture of fluids through said microfluidic device, in order to obtain an analysis of said fluid to be analyzed.

The method of use measures at least one medically relevant property of said sample, and the device is cleaned for reuse by flowing a diagnostic fluid through the device. Moreover, said diagnostic fluid may contain means for analysis of more than medically relevant property of said sample. The pressure drop across said device, when used in the method, is less than about 5 psi or its equivalent in SI units.

In another aspect of the invention, a system for clinical analysis comprises an inlet for a clinical sample, and inlet means for at least one diagnostic reagent, and a mixer for said sample and said reagent, said mixer comprising a spiral flow path to provide partial mixing of said sample and said reagent, and a vortex mixer to provide partial mixing of said sample and said reagent, and detection means for detecting the reaction of said sample with said reagent, and is characterized in that both said spiral mixing and said vortex mixing are required to provide sufficient mixing to provide a reproducible value for said detection.

The current invention is directed to the mixing of sample and analytical reagents in a microfluidic clinical analysis system. One challenge of a clinical assay system is to achieve effective mixing of clinical samples, such as blood or other body fluids, with analytical reagents. In systems using large volumes of reagents per test—for example, a milliliter or more—there are many simple devices available, such as shaking together solutions in a test tube or syringe. But for smaller volume systems, sample handling is more difficult.

The system of the invention, which is adapted for portability and field use, uses clinical samples on a "finger-prick" scale, equivalent to a drop of blood, some of which is drawn up by capillary action into a micropipette or other small-volume container. This is how a sample is presently acquired for a hematocrit, but most tests for metabolic and other non-physical standards are typically done on samples taken and analyzed at larger scales. This is simpler in terms of mixing and handling, but requires practical experience in phlebotomy to obtain a sufficiently large sample from the circulation.

Thus, while there are suitable systems now available for regular blood sampling and analysis in doctor's offices and hospital laboratories, there is no good alternative for equivalent sampling and analysis at remote sites. In response to this unmet need, the present device is being developed for use in space operations, such as a voyage to Mars. Moreover, many potential uses at remote or otherwise isolated locations on earth are contemplated.

The present invention provides a method for reliably mixing a small volume of blood, for example less than about 100 microliters, with a diluent. The diluent may be intended either for simple dilution, or for mixing with reagents in the diluent. While mixing is possible on a larger scale with a Vortex-type mixer or similar device, it is much more difficult when a few microliters are being dispensed.

A second need for use at remote sites is to have a handling system for blood and other samples that minimizes waste volume and exposure. In this regard, the current procedure of simply diluting some blood with saline or reagent, for example 50 microliters of blood with 5 ml of reagent solution, and applying some of the mixture to a current model analytical system, is less than optimal. Human blood is now treated as a potential biohazard, and so, besides being potentially wasteful of reagents, significant volumes of potentially hazardous materials are created by many current procedures.

In the present invention, it is demonstrated that efficient mixing can be obtained by use of an innovative spiral mixer, preferably combined with rotational vortex mixing after initial dilution. The mixer can be constructed as a single piece device, and can be made to be self-cleaning and re-useable. Because the mixer is reusable, its increased complexity (compared to a test tube) does not significantly affect assay costs.

Figure 1:
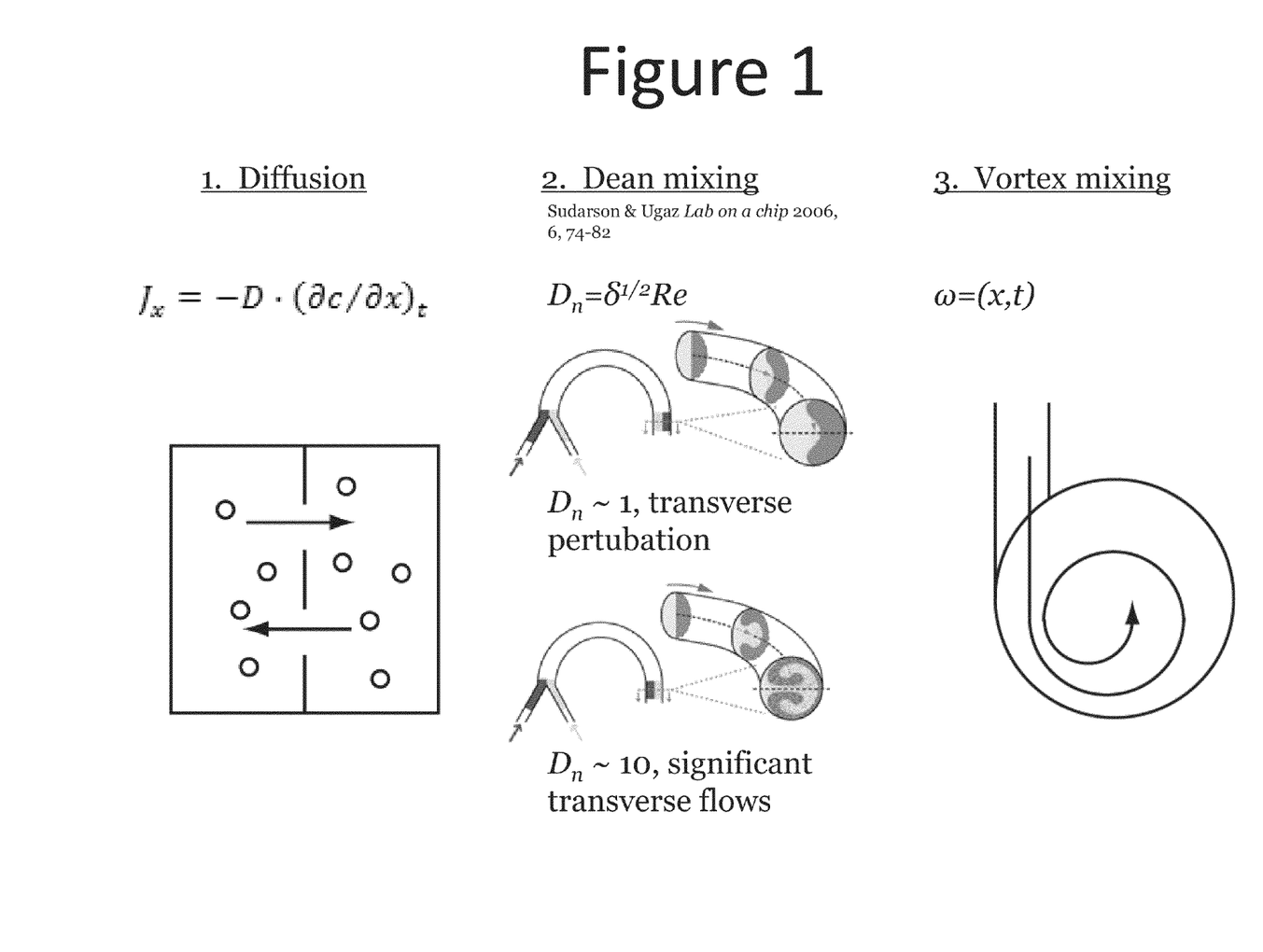
FIG. 1 shows the three mixing processes involved in the invention.

FIG. 1 illustrates three mixing modalities that are in action in the device. The first is simple diffusion, illustrated schematically in the left panel. Diffusion through a membrane is illustrated, but the principle is the same in a solution being exposed to a different solution. Diffusion is proportional to the diffusion coefficient of the species, and to the concentration gradient of the species.

The second panel illustrates "Dean Mixing", which supplements diffusional mixing of two contacting fluids when a flow path is curved, for example in a spiral. In essence, a parcel of fluid is stretched, from an initial straight bolus into a curved shape, and eventually into a substantially mixed state.

The third panel illustrates a form of "toroidal" or "vortex" mixing, in which a fluid with a significant velocity is emitted from a first passage into a second passage, usually with a significant increase in diameter. Above Reynolds numbers greater than about 2000, flow becomes turbulent rather than laminar. This produces rapid mixing; however, the turbulence is accompanied by a significant pressure drop, which is undesirable. In the invention, vortex mixing is used in a laminar (non-turbulent) flow rate range.

The fourth mode of mixing, an out-of-plane drop, approximately equivalent to a right-angle bend with little diameter change, is a convenient way to create Dean vortexes, given the small radius of curvature, which is inversely proportional to the strength of the transverse flow.

Figure 2:
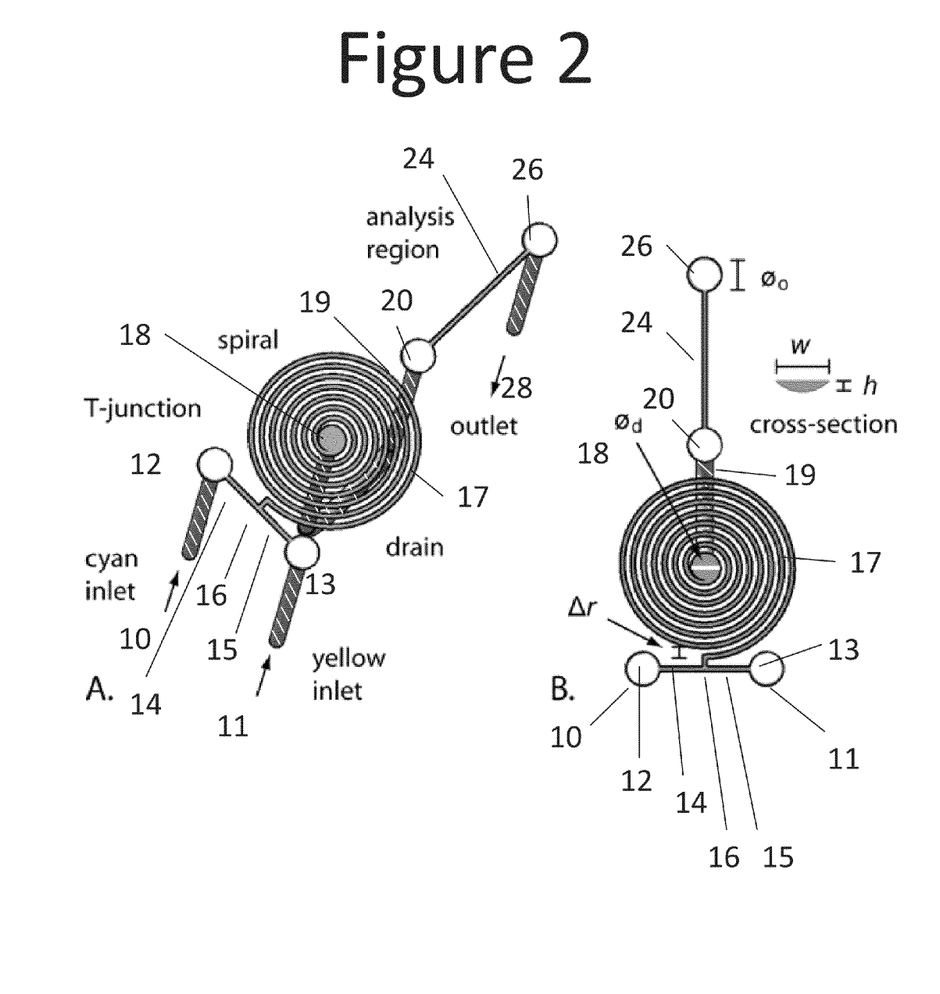
FIG. 2 shows a first layout of a spiral vortex mixer of the invention.

In a preferred embodiment, the spiral mixer of the invention combines Dean mixing with vortex mixing to obtain thorough mixing with low overall system pressure drops. A spiral vortex mixer of the invention is shown in FIG. 2. In this embodiment, the flow-directing fluid passages of the device are drawn as being comprised of tubular structures. In an alternative method, especially suitable for mass production, the passages are made by creating pathways in glass or polymeric sheets or blocks, by molding, etching or other fabrication procedure. Once the passages have been formed, the various sheets or blocks are then joined by bonding. Such a device could also be made in part of free standing tubing.

The mixer has two inlets, 10 and 11, respectively for blood (or other analyte) and saline or other diluent. These are respectively connected to chambers 12 and 13, and pass through narrow channels 14, 15 to meet at T-junction 16. The inlet into tube 16 is shaped to allow substantially laminar flow of sample and reagent, at a range of angles of input. In this embodiment, the tubing diameter downstream of junction 16 is smaller than the combination of the inlet tubes 14 and 15, and so initial flow in tube 16 is approximately laminar, so that the fluids mix only by diffusion.

The fluids make a right angle bend when exiting tube 16, and enter the spiral 17. (Some mixing occurs at this bend.) While fluid is flowing through spiral 17, it is undergoing Dean-type mixing, shown schematically in cross section at panel 25. This mixing is a result of the curvature of the spiral 17, in which the "inside" track (here, with blood) has a shorter path to travel than the "outside" track, here saline. The resulting shear sets up weak vortexes which mix the reagents much faster than diffusion, but with relatively low turbulence. In a short spiral, as illustrated (about 3 complete turns), it is not expected that complete mixing of the fluids will occur before the flows leave the Dean-effect spiral.

Fluid flowing in through the spiral path 17 eventually reaches tube 18, where a second mixing step occurs. The fluids enter the tube 18 tangentially, at a right angle with respect to the length of tube 18, and spiral around the outside of tube 18. The fluids continue to spiral as it sinks downwards in tube 18. The rotational vortex pattern is shown at 26, which is a schematic view of the path of a volume as it passes from the top of drain 18 down to the bottom. This rotational vortex mixing completes the mixing of the two components.

Tube 18 will often have a diameter larger than the local diameter of the spiral flow path 17, which aids in creating the rotational vortex 26. The tube 18 connects via an outlet 19 to a passage 20. Passage 20 connects the inner end of the spiral to a tube 21 and an outlet 22 from the mixing system. (These features are variable depending on the detailed design of the particular system.) From the outlet 22, the fluid passes through a detection channel 23, where optical measurements of the flow are made. Fluid finally exits at outlet 24. Other arrangements of this terminal region are possible.

For a sense of scale, in one embodiment of the invention the chambers 12 and 13 are approximately 2 mm in maximal diameter (or other cross section). The thin passages of the spiral 17 and analysis region 24 can be about 0.2 to 2 mm in maximal cross section dimension. Neither the passages nor the chambers are necessarily circular in cross-section and may be open channels in one or more planes, closed by bonding to a planar surface or other means. Other channel diameters, and ratios of diameters or characteristic sizes, can be used in the invention.

As an example, mixers of the invention can be made by etching a combination of slides. A "slide" in this description is a generally planar object, similar to a microscope slide— preferably transparent at least in part, having a shape generally similar to a microscope slide, but often smaller in dimensions (for example, 20 by 40 by 4 mm). In a first slide, pathways and chambers are formed by etching (for example, by one or more chemicals and/or a laser) into a first (upper) surface of a first slide. Inlets like 10 and 11, formed by etching or other means, pass through the first slide, A second slide, which may be thinner, can be bonded to the first, upper surface of the first slide. The inlets 10, 11 and the outlet 24 remain accessible at the lower surface of the first slide.

The fluids that enter the inlets combine at junction 16 and then flow, in a generally laminar way, to the first drain 18. The passage 19 leading from drain 18 to chamber 22 can be constructed by any convenient means that provides proper connectivity. For example, passage 19 could be cut in the lower surface of the slide, sealed by another slide or a thinner layer ("coverslip"; not shown) and be connected via a vertical section to chamber 22. In another embodiment, chambers equivalent to chambers 18 and 22 are connected by a passage to the lower face of the slide, and passage 19 is a piece of tubing connecting those two chambers.

In a current embodiment, the slides are made of glass, and are bonded together by plasma bonding. Other compositions and adhesives are possible, and may be preferred, especially in high volume manufacturing. Parts can be made by injection molding, or by stamping of plastic materials, or by other known high-volume processes. A further advantage of the invention is that the mixing and analysis assembly is not necessarily a one-use device, but can potentially be cleaned in situ (or in a specialized cleaning device) and used for additional assays. This is an important advantage in remote locations.

In a preferred mode of usage, when volumes of reagent used are not a concern, the microfluidic system can run a diluent continuously and inject samples at intervals, to facilitate automatic data processing of optical or other signatures of the well-mixed stream.

Figure 3:
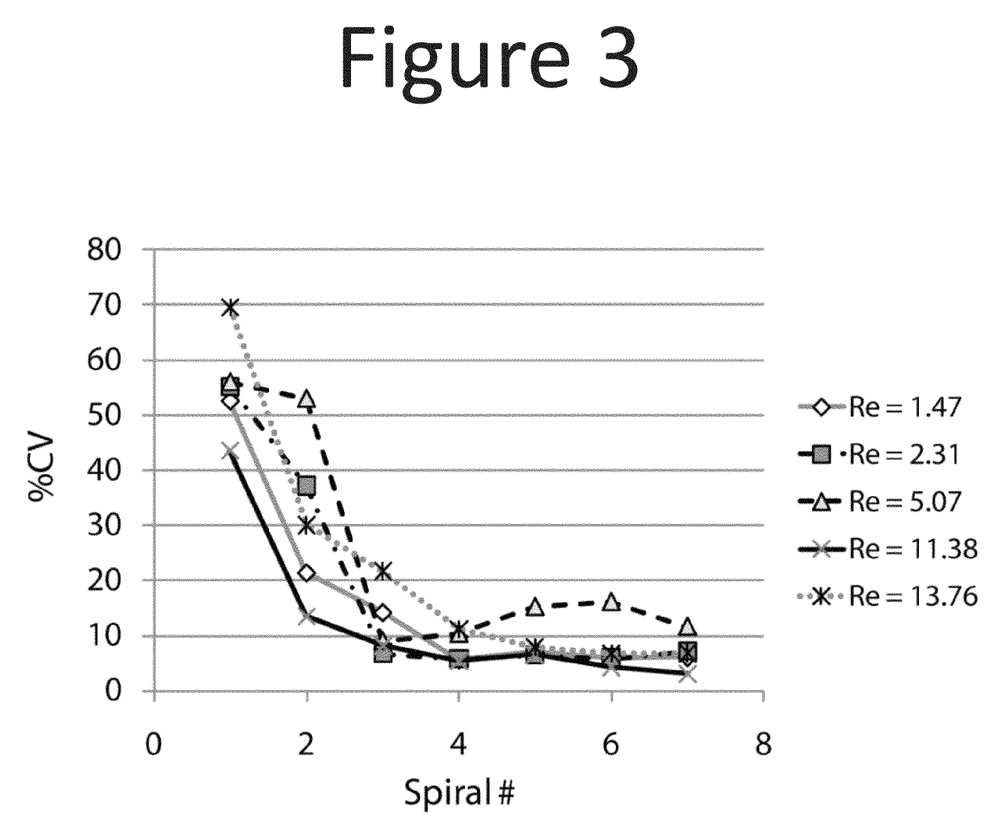
FIG. 3 shows visualizations of some of the mixing forces.

A plot of relative mixing in a seven turn spiral channel (similar to the three turn spiral in FIG. 2) is shown in FIG. 3A, in an apparatus similar to that of FIG. 2. A three turn or four turn spiral appeared to produce optimal mixing at a variety of Reynolds numbers Re. FIG. 3A also shows the effective mixing of two streams within the device at various pressures as the streams pass various numbers of spirals. The proportion of the streams not mixed (% CV) plateaus at about 3 turns of the spiral and does not improve significantly with pressures above about 2 psi. Likewise, FIG. 3B shows a vortex mixing step without previous spiral mixing, showing that a single vortex alone can be insufficient to mix two streams.

Minimization of pressure required to mix the sample with the diluent is important, because inexpensive portable pumps that are preferred for these devices have low limits on the pressure they can apply, for example less than about 7.5 psi (pounds per square inch; ca. 0.5 atm). Low pressure is also important for safety, especially in remote or otherwise uncontrolled or uninspected environments.

Figure 4:
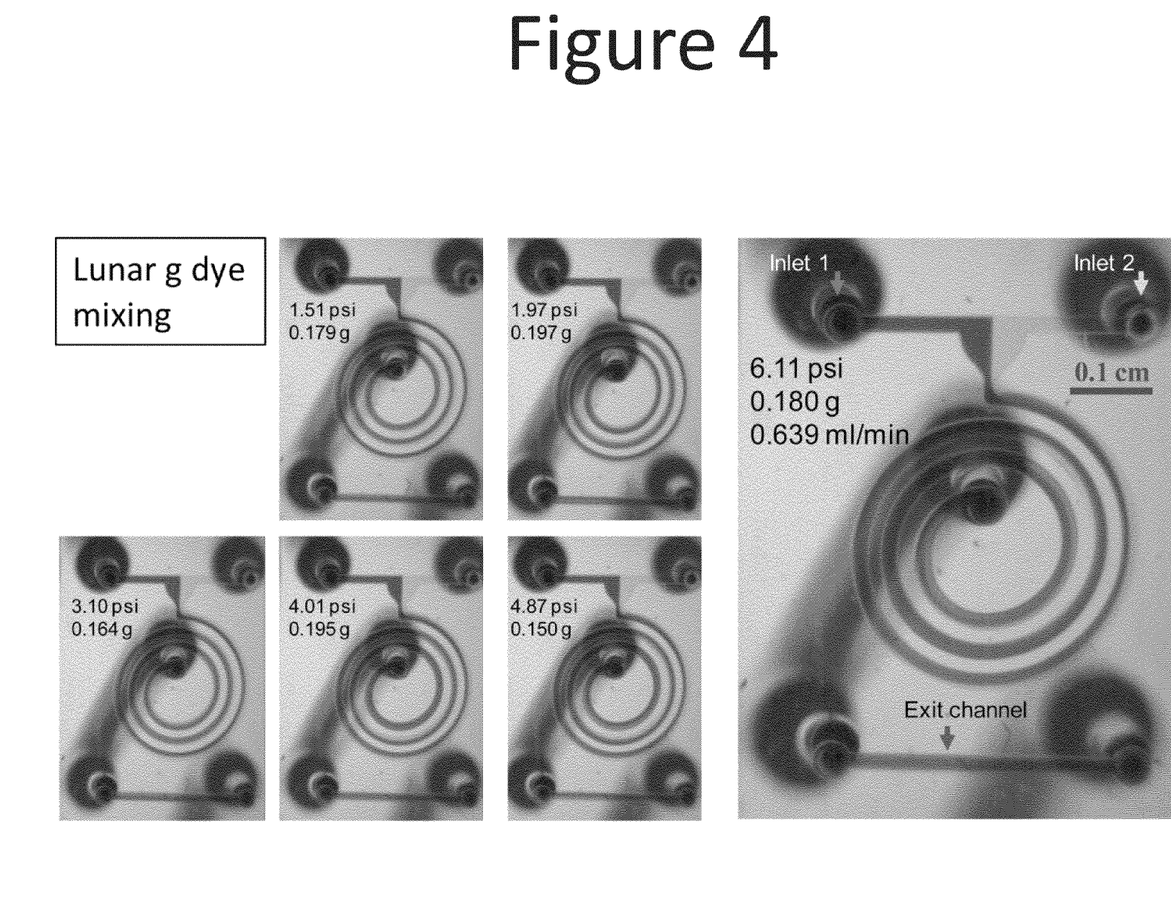
FIG. 4 shows flows in a spiral at varying pressures.

FIG. 4 shows a spiral dilution apparatus of the invention, similar to FIG. 2, but having fewer turns of the spiral loop—in this case, three rather than seven. The pressures required to obtain various flow rates are shown. It is found that pressure differentials as high as 6 psi fail to completely mix the dye samples before they exit from the spiral. However, pressures of 3 psi and above provide significant mixing in the chambers. In these devices, mixing also occurs when the flow channel expands into a larger area, such as chambers 12, 13, 18, 20 and 26 of FIG. 2, and in larger diameter channels, such as outlet region 19.

It also can be seen in FIG. 4 that while mixing in the spiral alone is not complete even at 6 psi, mixing in the exit channel/ analysis region 24 appears to be complete at pressures of 3 psi and above, and possibly lower. It is also clear that mixing in the drain chamber 18 (FIG. 2) alone is not sufficient to finish the mixing of the fluids in the spiral channel.

Figure 5:
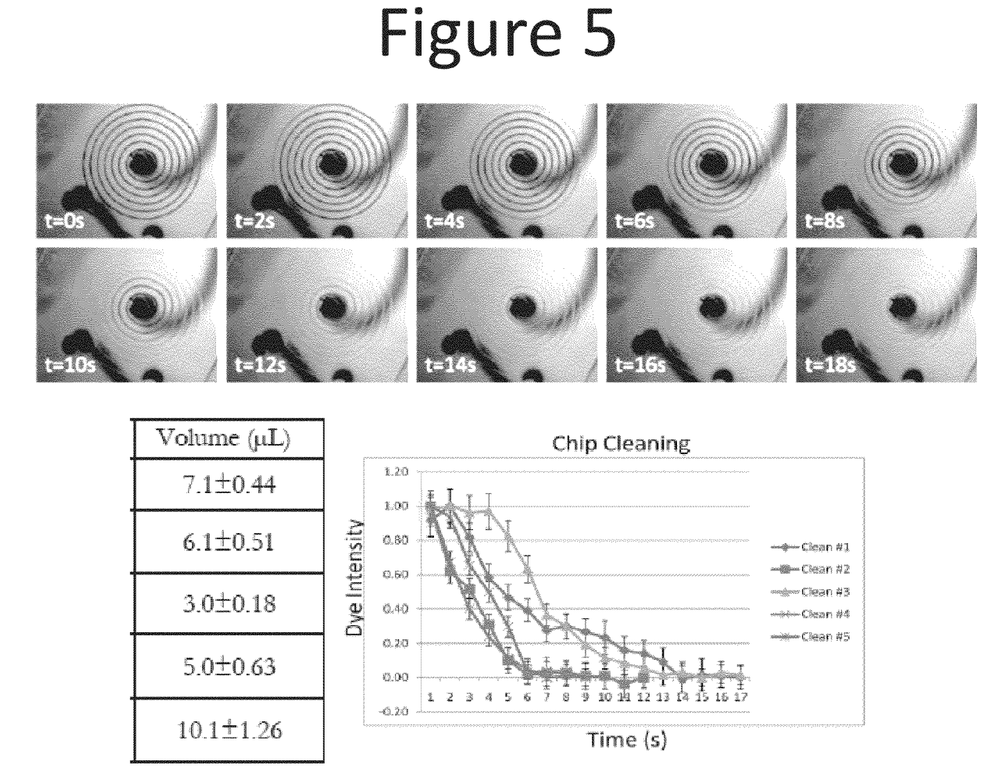
FIG. 5 shows the rapid cleaning of the device of the invention during flushing.

FIG. 5 shows the cleaning of a spiral dilution apparatus of the invention, after its use for a first assay. The spiral path (thin nearly circular channels), which is filled with fluid containing dye, is easily seen at the beginning, but the dyed fluid is sufficiently well mixed and extracted to be effectively invisible with only 20 seconds of cleaning flow.

Figure 6:
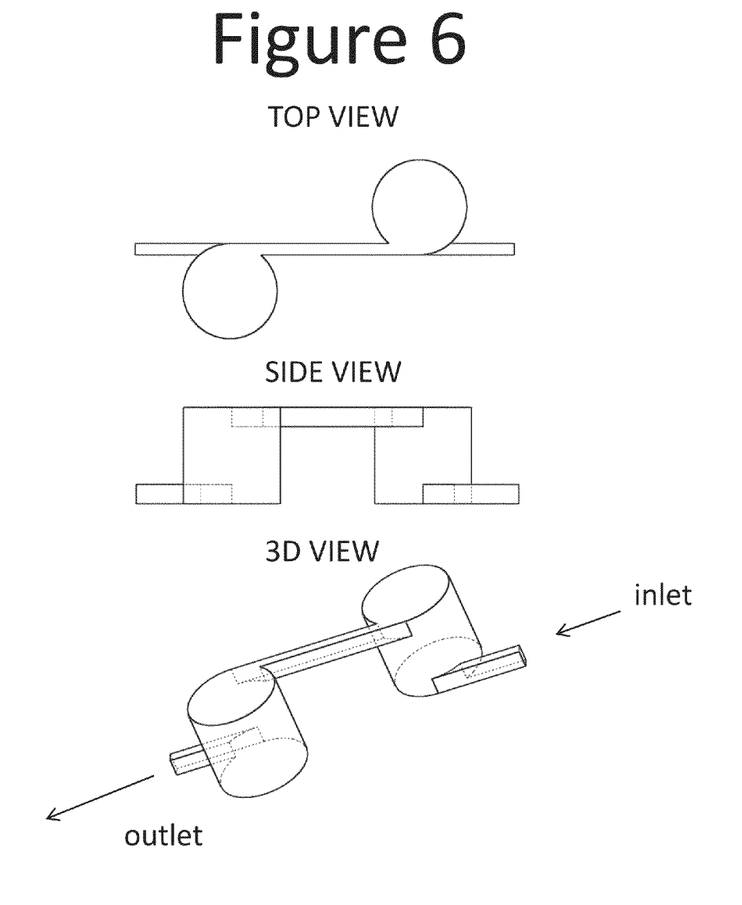
FIG. 6 shows a different embodiment with two serial 3-D vortices.

In FIG. 6, the diagram shows two rotational vortices in series. In particular, this describes two serial counter-rotating vortexes in series with one another. The sample to be mixed enters one of the inlets, then goes through the first rotational vortex in one direction (i.e. left- or right-handed rotation) and then enters the second rotational vortex in the opposite orientation. This approach allows for rotation and counter-rotation of the sample and is consistent with subjecting the sample to at least two different mixing forces to attain good mixing.

Thus, the combination of spiral flow Dean-type mixing and mild vortex-type mixing in the chambers produces a result that cannot readily be obtained by either type of mixing alone, and at a significantly lower pressure differential across the apparatus compared to complete mixing that is purely of either type. The microfluidic device of claim 1 wherein said microfluidic mixing device has an inlet shaped to allow substantially laminar flow of said sample and said reagent.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference, where such incorporation is permitted. Nothing herein is to be construed as an admission that the invention is not entitled to antedate such disclosure by virtue of prior invention, where relevant. Those skilled in the art will recognize, or be able to ascertain using no more than routine experimentation, many equivalents to the specific embodiments of the invention described herein. Such equivalents are intended to be encompassed by the following claims.

The invention claimed is:

1. A microfluidic mixing device for mixing a flow of sample with a flow of diagnostic reagent, characterized in having reliable mixing and flow at low pressure drop, wherein the device comprises:
   a first vortex mixer, wherein partial mixing is accomplished by rotational vortices; and
   at least one of:
      a spiral channel sharing a channel with the first vortex mixer, wherein partial mixing is accomplished by Dean vortices; and
      a second vortex mixer sharing a channel with the first vortex mixer and having opposite handedness than said first vortex mixer, wherein partial mixing is accomplished by rotational vortices.

2. The microfluidic mixing device of claim 1 wherein said vortex mixing is at approximately right angles to the plane of the spiral.

3. The microfluidic mixing device of claim 1 wherein a form of vortex mixing is found in more than one place in said microfluidic mixing device.

4. The microfluidic mixing device of claim 1 wherein said second section comprises more than one vortex mixing site.

5. The microfluidic device of claim 1 wherein said microfluidic mixing device is capable at operating at a differential pressure of less than about one half of atmospheric pressure.

6. The microfluidic mixing device of claim 1 further comprising an outlet leading to an analysis region.

7. The microfluidic device of claim 1 wherein said microfluidic mixing device further comprises mixing at three or more mixing sites in the flow path, said mixing sites comprising at least one rotational a vortex-type mixing site and at least one Dean vortex-type mixing site.

8. The microfluidic device of claim 1 wherein said microfluidic mixing device is reusable.

9. The microfluidic device of claim 1 wherein said microfluidic mixing device has an inlet shaped to allow substantially laminar flow of said sample and said reagent.

10. The microfluidic device of claim 1 wherein said diagnostic reagent reacts to a plurality of medically relevant properties of said sample.

11. The microfluidic device of claim 1 wherein said spiral is upstream and said second section comprises a vortex mixer into which said sample enters tangentially.

12. The device of claim 1 wherein there is more than one inlet for introducing fluids into said device.

13. The microfluidic device of claim 1 further comprising means for metering different ratios of diluent into said device.

14. A method of analysis of clinical samples, the method comprising the steps of:
   connecting a first inlet to a supply of a diagnostic fluid; and
   connecting a second inlet to a sample to be analyzed;
   wherein said first and second inlets are connected to a set of microfluidic mixing devices for mixing a sample with a reagent;
   characterized in that the microfluidic mixing devices comprises a first vortex mixer that accomplishes partial mixing using rotational vortices, and at least one of a Dean vortex-type mixer and a second vortex mixer of opposite handedness to said first mixer that accomplishes partial mixing using rotational vortices.

15. The method of claim 14 further comprising,
   providing a third section downstream of both said first section and said second section or sections, said third section containing one or more devices to perform at least one analysis on the mixture of the fluids from said first and second inlets; and
   passing said mixture of fluids through said microfluidic device, in order to obtain an analysis of said fluid to be analyzed.

16. The method of claim 15 wherein said analysis measures at least one medically relevant property of said sample.

17. The method of claim 15 wherein said device is cleaned for reuse by flowing a diagnostic fluid through the device.

18. The method of claim 15 wherein said diagnostic fluid reacts to a plurality of medically relevent properties of said sample.

19. A system for clinical analysis wherein said system comprises:
   an inlet for a clinical sample;
   inlet means for at least one diagnostic reagent;
   at least two mixers to mix said sample and said reagent, said mixers comprising:
      at least one vortex-type mixer to partially mix said sample and said reagent using rotational vortices; and
      at least one additional mixer to partially mix said sample, wherein said second mixer is one or more of a second vortex mixer using rotational vortices to partially mix said sample, and a spiral mixer using Dean vortices to partially mix said sample; and
   detection means for detecting the reaction of said sample with said reagent.

* * * * *